United States Patent
Lopez

(10) Patent No.: US 9,795,508 B2
(45) Date of Patent: Oct. 24, 2017

(54) OCULAR INFUSION SYSTEM

(71) Applicant: Alcon Research, Ltd., Fort Worth, TX (US)

(72) Inventor: Jose Lopez, Cypress, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 479 days.

(21) Appl. No.: 13/669,971

(22) Filed: Nov. 6, 2012

(65) Prior Publication Data
US 2014/0128847 A1    May 8, 2014

(51) Int. Cl.
| | | |
|---|---|---|
| *A61F 9/007* | (2006.01) | |
| *A61M 39/08* | (2006.01) | |
| *A61M 39/10* | (2006.01) | |
| A61M 5/32 | (2006.01) | |
| A61M 5/158 | (2006.01) | |

(52) U.S. Cl.
CPC ......... *A61F 9/00781* (2013.01); *A61M 39/08* (2013.01); *A61M 39/10* (2013.01); *A61M 5/329* (2013.01); *A61M 2005/1581* (2013.01); *A61M 2210/0612* (2013.01)

(58) Field of Classification Search
CPC .................. A61M 39/08; A61M 39/10; A61M 2005/1581; A61M 2005/341; A61M 2210/0612; A61M 5/158; A61M 5/1586; A61M 5/346; A61M 5/329; A61M 5/3286; A61M 2025/0175; A61F 9/0008; A61F 9/0017; A61F 9/0026; A61F 9/00781; A61B 2017/00991
See application file for complete search history.

(56) References Cited

U.S. PATENT DOCUMENTS

| | | | | |
|---|---|---|---|---|
| 2,187,259 | A * | 1/1940 | Barnhart ................. | A61M 5/32 604/117 |
| 3,884,238 | A * | 5/1975 | O'Malley et al. ............ | 606/107 |
| 3,906,946 | A * | 9/1975 | Nordstrom ........ | A61M 25/0637 604/165.03 |
| 4,452,599 | A * | 6/1984 | Albisser et al. .............. | 604/500 |
| 4,781,675 | A * | 11/1988 | White ................... | A61F 9/0017 604/10 |
| 4,813,939 | A * | 3/1989 | Marcus ............. | A61M 39/0208 604/174 |
| 5,409,457 | A * | 4/1995 | del Cerro ............ | A61F 9/00736 604/117 |
| 5,468,230 | A * | 11/1995 | Corn ............................. | 604/180 |
| 6,004,302 | A * | 12/1999 | Brierley .............. | A61F 9/00781 604/239 |
| 6,551,291 | B1 * | 4/2003 | de Juan et al. ................ | 604/294 |
| 6,748,786 | B2 * | 6/2004 | Ooyauchi ............. | B21C 37/065 428/577 |
| 2008/0097387 | A1 * | 4/2008 | Spector ........................ | 604/512 |
| 2012/0095404 | A1 * | 4/2012 | Massengale et al. .... | 604/164.01 |

* cited by examiner

*Primary Examiner* — Theodore Stigell
*Assistant Examiner* — Benjamin Koo

(57) ABSTRACT

Systems, processes, and articles of manufacture may be used to perform ocular infusion. In particular implementations, a system for ocular infusion may include a length of flexible tubing and a tip adapted to be inserted into an eye. The flexible tubing may be adapted to convey an ocular infusion fluid and include a plurality of coils set in at least a portion thereof. The ocular tip may be coupled to a first end of the flexible tubing and adapted to convey ocular infusion fluid from the flexible tubing into an eye.

15 Claims, 5 Drawing Sheets

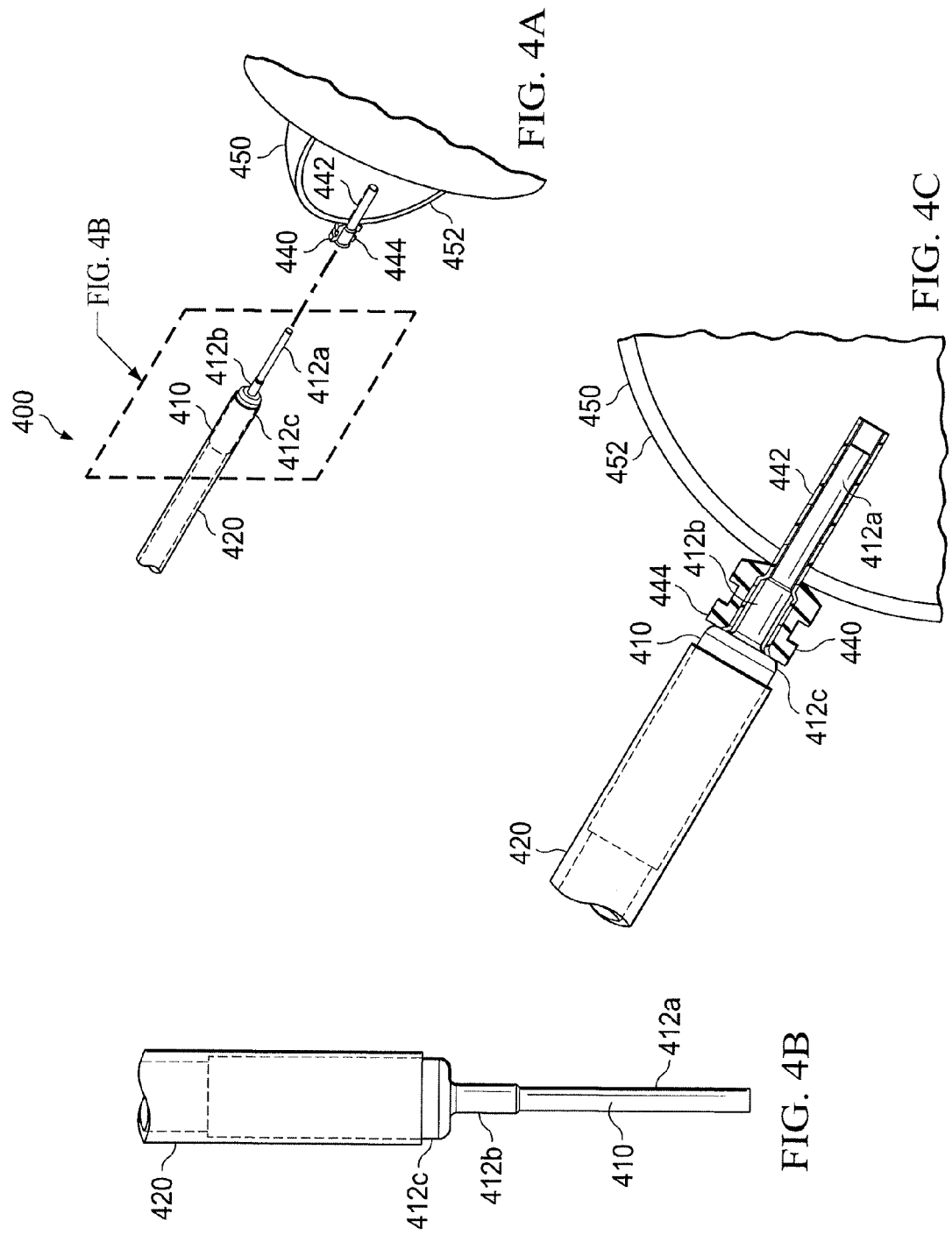

OCULAR INFUSION SYSTEM

TECHNICAL FIELD

The present disclosure relates to optical surgery, and more specifically to infusing fluid into a patient's eye.

BACKGROUND

The human eye, in simple terms, functions to provide vision by transmitting and refracting light through a clear outer portion called the cornea and focusing the image by way of the lens onto a light-sensitive tissue lining the inner surface called the retina. The quality of the focused image depends on many factors including the size, shape, and length of the eye, and the shape and transparency of the cornea and lens.

Unfortunately, trauma, age, or disease may cause a variety of problems with the eye (e.g., cataracts or retinal detachment). However, many surgical procedures have been developed that allow repair to various part of the eye (e.g., lens and retina). During these surgeries, fluids may need to be introduced into the eye (e.g., to maintain intraocular pressure or to manipulate eye components). These fluids are typically introduced through cannulas, which are basically long, straight tubes that are inserted into the eye.

SUMMARY

In one general implementation, a system for ocular infusion may include a length of flexible tubing and a tip adapted to be inserted into an eye. The tubing may be adapted to convey an ocular infusion fluid and include a plurality of coils set in at least a portion thereof. The tip may be coupled to a first end of the flexible tubing and adapted to convey ocular infusion fluid from the flexible tubing into an eye.

In certain implementations, the flexible tubing may be composed of silicone. The flexible tubing may also include straight portions at both ends of the coiled portion.

In some implementations, the tip may include a first portion and a second portion. The first portion may be adapted to be inserted into an eye, and the second portion may be adapted to remain outside the eye and include a bend, such as, for example, a 90 degree bend. In some instances, the bend may be within the range of 90 degrees and 180 degrees. The first portion may, for example, be composed of metal, and the second portion may be composed of plastic. In particular implementations, the second portion may be adapted to receive the first portion.

Certain implementations may include a second length of flexible tubing and a coupler. The coupler may be adapted to couple to a second end of the first length of flexible tubing and to a first end of the second length of flexible tubing.

Various implementations may include one or more features. For example, while assisting with maintaining intraocular eye pressure, which prevents an eye undergoing surgery from collapsing, an ocular infusion system may provide increased room for a user (e.g., physician or other medical professional) to operate during a surgery. During certain surgeries, for example, a user may have to manipulate an eye (e.g., to reach various locations), and having increased room may facilitate these manipulations. As another example, the coils of a flexible tubing may allow an ocular tip to be placed at varying orientations (e.g., during eye manipulation) without increasing torque on the eye, which may result in less trauma to the eye.

The details and features of various implementations will be conveyed by the following description, along with the drawings.

DESCRIPTION OF THE DRAWINGS

FIGS. 4A-C illustrate exploded and cross-sectional views of an example ocular infusion system in use.

DETAILED DESCRIPTION

Figure 1A:
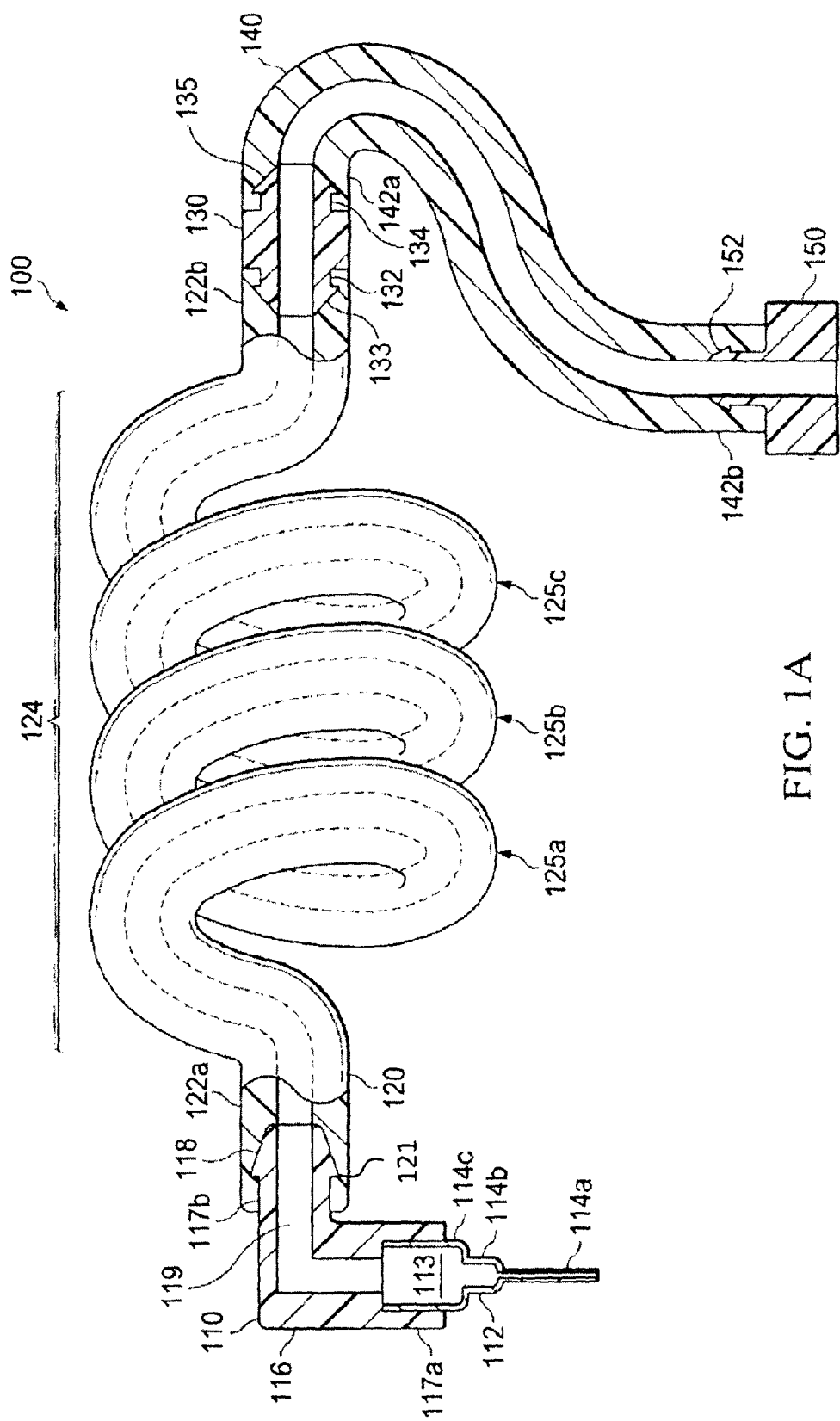
FIG. 1A shows an example system for ocular infusion.
Figure 1B:
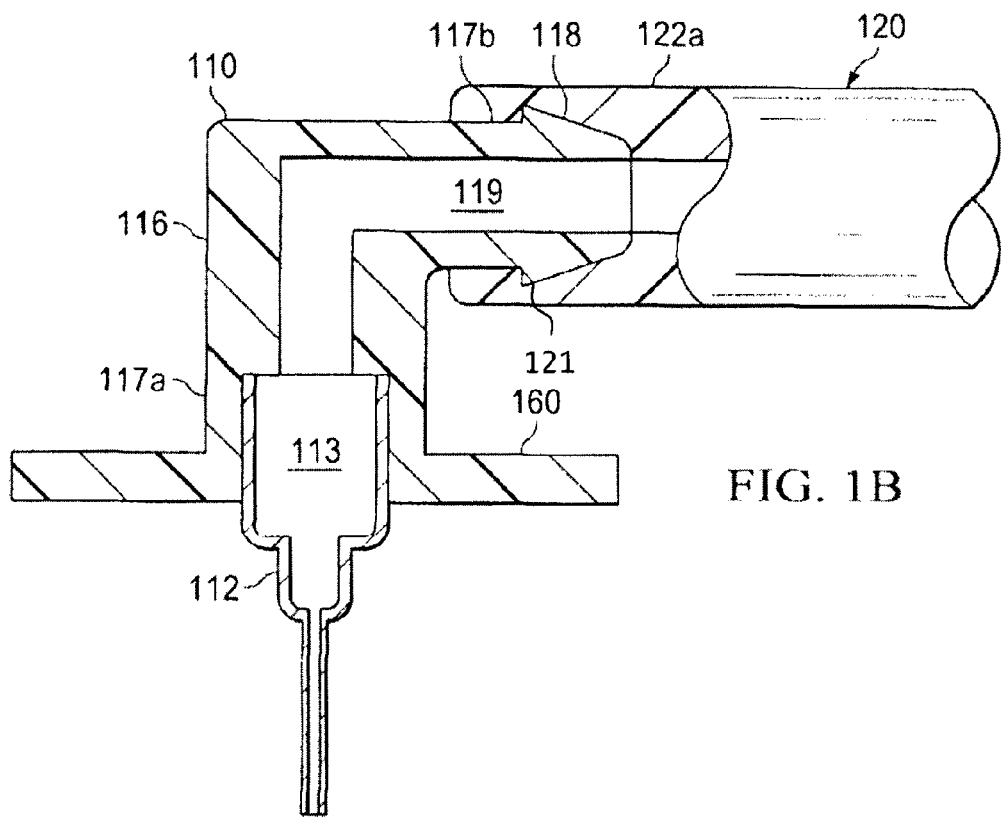
FIG. 1B shows an partial view of another example system in which the second portion includes a flange extending from a distal end thereof.
Figure 1C:
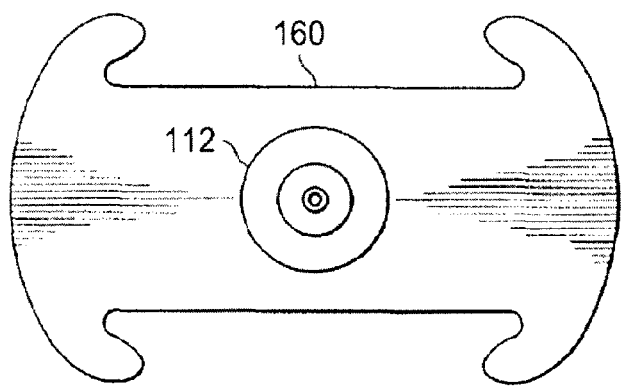
FIG. 1C shows a bottom view of the example system of FIG. 1B.

FIG. 1 A illustrates an example system 100 for ocular infusion. System 100 includes an ocular tip 110, a first length of flexible tubing 120, a first coupler 130, a second length of flexible tubing 140, and a second coupler 150. System 100 may, for example, be useful for infusing a fluid (i.e., liquid or gas) into a patent's eye during surgery to maintain the eye's shape. Fluid may, for example, leak from the eye during surgery due to incisions, and if the eye loses too much fluid, it may collapse. Normal intraocular pressure is typically between 10-20 mmHg, but, during surgery, the pressure can range from 0-120 mmHg.

Ocular tip 110 includes a first portion 112 that is adapted to be inserted into an eye and a second portion 116 that is adapted to couple to flexible tubing 120. First portion 112 includes three sections 114a through 114b. First section 114a is adapted to be inserted into an eye. The first section 114 may be inserted directly into the eye or through another device (e.g., a trocar cannula). Second section 114b is wider than first section 114a, and third section 114c is wider than second section 114b and provides a mounting interface for coupling first portion 112 to second portion 116. In some implementations, the third section 114c may include an internal annular recess adapted to receive the ocular tip 110. Further, for implementations with or without the recess, the first portion 112 may be retained within the first section 117a of the second portion 116 by an interference fit. First portion 112 also includes a passage 113 that is formed by the insides of sections 114a, 114b, and 114c. Passage 113 allows infusion fluid to flow through first portion 112 and into an eye.

First portion 112 may be made of various materials. In particular implementations, for example, first portion 112 may be made of metal (e.g., stainless steel or gold). In other implementations, first portion 112 may be made of any other appropriate material.

First portion 112 may be made by various processes. In certain implementations, for example, first portion 112 may be made by being drawn from a stock piece. The drawing process may create the necking between sections 114 of first portion 112. In other implementations, first portion 112 may be made by other processes.

Second portion 116 includes a first section 117a and a second section 117b. First section 117a is adapted to receive third section 114c of first portion 112. First portion 112 and second portion 116 may be coupled to each other at the interface between first section 117a and third section 114c by various techniques (e.g., friction fit, bonding, or snap fit).

Second section 117b includes a coupling mechanism 118 for engaging flexible tubing 120. In this implementation, coupling mechanism 118 includes a barb 121 adapted to provide resistance to flexible tubing 120 moving away from second portion 116. Other mechanisms may also be used.

As illustrated, first section 117a and second section 117b have an angle between their longitudinal centerlines. In the example implementation shown in FIG. 1A, the angle is approximately 90 degrees. In other implementations, other angles may be used. For example, in some implementations, the angle may be less than 90 degrees. In still other implementations, the angle may be greater than 90 degrees. Thus, the angle between the centerlines of the first section 117a and the second section 117b may be selected to be any desirable angle. Additionally, the first section 117a and the second section 117b define a passage 119 that extends through second portion 116. In some instances, passage 119 is adapted to convey infusion fluid from flexible tubing 120 to first portion 112. In other instances, passage 119 is adapted to convey fluid from the first portion 112 to the flexible tubing 120.

Second portion 116 may be made of various materials. In particular implementations, for example, second portion 116 may be made of plastic (e.g., through an injection molding process). In other implementations, second portion 116 may be made of any other appropriate materials.

In particular implementations, first portion 112 may be approximately 0.375 inches in height, second portion 116 may be approximately 0.25 inches in height, and ocular tip 110 may be approximately 0.5 inches in height when assembled. In other implementations, the components may have different sizes. That is, the first portion 112, second portion 116, and ocular tip 110 may have any desired size.

In some implementations, ocular tip 110 may introduce fluid into an eye through a trocar cannula, which may serve as a port for introducing various instruments and/or fluids into an eye. In these implementations, one or more portions of ocular tip 110 (e.g., first section 114a and second section 114b) may be sized to fit inside a trocar cannula, and another portion (e.g., third section 114c) may be sized to abut the trocar cannula. In some implementations, ocular tip 110 may introduce fluid directly into an eye (e.g., by first section 114a being inserted through the sclera).

In particular implementations, ocular tip 110 may include a flange 160, as shown in FIG. 1B. The flange 160 is operable to prevent ocular tip 110 from penetrating too far into the eye. In some instances, the flange 160 may define suture plates that are also adapted to secure the second portion 116 to the eye to immobilize the ocular tip 110 relative to the eye. In the example shown, the flange 160 extends from a distal end of the first section 117a. The flange 160 may, for example, be made of plastic.

Flexible tubing 120 includes a first end 122a, which is coupled to ocular tip 110, a second end 122b, which is coupled to the first coupler 130, and a coiled portion 124. As illustrated, coiled portion 124 includes three coils 125a, 125b, and 125c. Coils 125a, 125b, and 125c are set in flexible tubing 120, meaning that the coils exist when flexible tubing 124 is in a quiescent state. Coiled portion 124 could include fewer or additional coils in other implementations.

Flexible tubing 120 may have a variety of sizes. For example, each of the first end 122a and the second end 122b may have a length within the range of 0.375 to 0.75 inches, which, in some instances, could provide a long, straight portion. In particular implementations, one or more of the coils 125a, 125b, and 125c may have an outside diameter of 0.5 inches, and the distance between adjacent coils may be about 0.375 inches. However, in other implementations, outer diameters of the coils may be larger or smaller than 0.5 inches, and the distance between adjacent coils may be larger or smaller than 0.375 inches. Thus, flexible tubing 120 may have other appropriate sizes in other implementations.

Flexible tubing 120 may be composed of various materials. In particular implementations, flexible tubing 120 may be composed of a material with thermal set properties. For example, the flexible tubing 120 may, in some implementations, be formed from silicone. In these implementations, the coils 125a, 125b, and 125c in flexible tubing 120 may, for example, be set by taking a length of straight tubing from an extruding device and wrapping a section of the tubing around a fixture that has the appropriate shape (e.g., a circular cylinder). In other implementations, the fixture may have any other desired shape. In some instances, the fixture, along with the tubing, may then be placed in an oven and baked for a length of time. For example, in some implementations, the tubing, along with the fixture, may be baked at a temperature between 300° F. to 400° F. for between two to four hours. However, the tubing and fixture may be baked for a temperature above or below the above range for a period of time that is greater or less than the above time span. This process of forming the coils may allow the tubing material to cross link further and maintain its shape when it is removed from the fixture. In other implementations, flexible tubing 120 may be composed of any other appropriate flexible material. In still other implementations, the coils 125a, 125b, and 125c may be formed in the flexible tubing 120 without the use of a fixture.

Coupler 130 is adapted to couple flexible tubing 120 to flexible tubing 140. Coupler 130 includes a first end 132 and a second end 134. First end 132 is adapted to fit inside second end 122b of flexible tubing 120 and includes an engagement mechanism 133 for engaging flexible tubing 120 to prevent it from moving away from coupler 130. In this implementation, engagement mechanism 133 includes an annular barb. In other implementations, other mechanisms could be used. Second end 134 is adapted to fit inside flexible tubing 140. Second end 134 also includes an engagement mechanism 135 for engaging flexible tubing 140 to prevent it from moving away from coupler 130. In this implementation, engagement mechanism 135 includes an annular barb. In other implementations, other mechanisms could be used.

The first coupler 130 may be made of various materials. In particular implementations, for example, coupler 130 may be composed of plastic. Particularly, in some implementations, the coupler 130 may be formed from polypropylene. Coupler 130 may be made of other appropriate materials in other implementations.

Flexible tubing 140 includes a first end 142a and a second end 142b. The first end 142a may be coupled to coupler 130. The second end 142b may be coupled to the second coupler 150. Flexible tubing 140 may be composed of various materials. In particular implementations, flexible tubing 140 may be composed of silicone. In other implementations, flexible tubing 140 may be composed of any other appropriate flexible material.

The second coupler 150 is adapted to couple to second tubing 140 to a fluid source. For example, the fluid source may be contained within a surgical console, and the coupler 150 may be adapted to couple to the surgical console. Coupler 150 may include an engagement mechanism 152 that engages second end 142b of second tubing 140 to prevent it from moving away from coupler 150. In some implementation, the engagement mechanism 152 may include an elongated barb that fits inside second end 142b, as shown in FIG. 1A. In other implementations, engagement mechanism 152 may have other configurations.

Coupler 150 may be composed of various materials. In particular implementations, coupler 150 may be composed of nylon. In other implementations, coupler 150 may be composed of any other appropriate material.

In certain modes of operation, system 100 assists with infusing a fluid (e.g., saline solution, air, or any other suitable gas or liquid) into an eye as surgery proceeds. The system 100 may introduce the infusion fluid into the eye directly or indirectly, such as via a trocar cannula. The infusion fluid may, for example, be supplied by a surgical console. The amount of infused fluid may, for instance, be established by a user (e.g., a physician or other medical personnel).

During or after surgery, system 100 may also assist with placing another fluid into the eye to facilitate holding components in place. For example, in some instances, the system 100 may be utilized to introduce a fluid such as air into the eye to assist in retaining a feature of the eye in position. For example, the system 100 may be used to assist holding an eye's retina in place. For example, system 100 may provide a venting path during silicone oil injection.

System 100 has a variety of features. For example, system 100 assists in maintaining intraocular eye pressure, which prevents an eye undergoing surgery from collapsing. As another example, system 100 may provide increased room for a user to operate during a surgery. During certain surgeries, a user may have to manipulate an eye (e.g., to reach various locations). Previous infusion systems, which typically extend from the eye at a normal (i.e., perpendicularly from the eye's surface) and require a service loop to prevent imparting forces to the eye, limit the room to perform such operations. Ocular tip 110, however, provides increase room for manipulation. Additionally, the coiled nature of flexible tubing 120 may allow ocular tip 100 to be placed at varying orientations (e.g., during eye manipulation) without increasing forces on the eye.

Although FIG. 1A illustrates one implementation of a system for ocular infusion, other systems for ocular infusion may have fewer, additional, and/or a different arrangement of components. In particular implementations, for example, first end 122a and/or second end 122b could include a long, straight portion. As another example, a system may not include a coupler 130 and/or second length of flexible tubing 140. For example, flexible tubing 120 may be adapted to couple to a fluid source. As a further example, ocular tip 110 may have other configurations or be composed of a uniform material.

Figure 2:
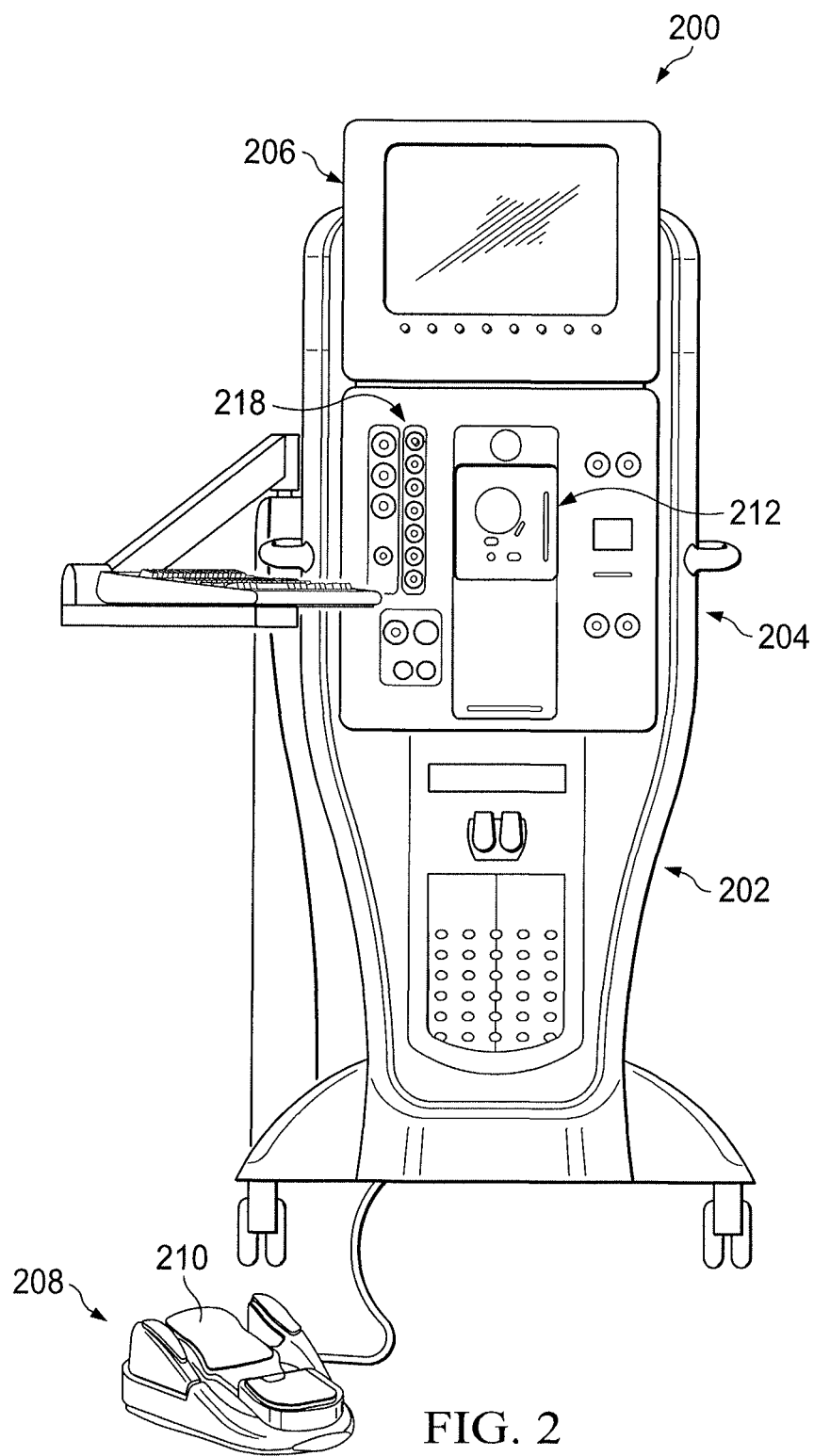
FIG. 2 shows an example surgical system for ocular surgery.

FIG. 2 illustrates an example surgical console 200 for ocular surgery. For instance, surgical console 200 may be a vitreoretinal surgical console from Alcon Laboratories of Fort Worth, Tex. Console 200 may, for example, be usable with system 100.

Console 200 includes a housing 202, a computer system 204, and a display 206 operable to show, for example, data relating to system operation and performance during an ocular surgical procedure. Display 206 may also interface with the console 200, such as to establish or change one or more operations of the console 200. In some instances, display 206 may include a touch-sensitive screen for interacting with the console 200 by touching the screen of the display 206.

Various probes may be used with console 200. A probe, such as, for example, a vitrectomy probe, may be coupled to console 200 for dissecting ocular tissues and aspirating the ocular tissues from the eye. Other probes may, for example, introduce fluids to and/or extract fluids from the eye. Console 200 may, for example, provide electrical, pneumatic, hydraulic, and/or other appropriate type of power to a probe. Console 200 may also be operable to control the supplied power (e.g., an infusion rate of fluid to a surgical site and/or aspiration of fluid from a surgical site), as well as to monitor one or more patient parameters.

Console 200 may also include a number of systems that are used together to perform ocular surgical procedures. For example, the systems may include a footswitch system 208 including, for example, a footswitch 210, a fluidics system 212, and a pneumatics system 218. The pneumatics system 218 may be operable to supply power to and control a probe. For example, the pneumatics system 218 may be operable to repeatedly cycle application of a pressurized gas. In some instances, the pneumatic system 218 may be operable to cycle pressurized gas at rates within the range of one cycle per minute to 7,500 cycles per minute. In some instances, the pneumatic system 212 may be operable to cycle pressurized gas at rates higher or lower than 7,500 cycles per minute. In certain implementations, the cycled gas may be applied at, for example, different pressures, different rates, and different duty cycles.

A probe may be interfaced with console 200 via pneumatics system 218 (e.g., to control actuation of a cutter). Fluidics system 212 may be operable to provide infusion and/or irrigation fluids to the eye or a vacuum, such as to aspirate materials during a surgical procedure. To optimize performance of the different systems during surgery, their operating parameters may be varied according to, for example, the particular procedure being performed, the different stages of the procedure, the surgeon's personal preferences, whether the procedure is being performed in the anterior or posterior portion of the patient's eye, and so on.

Fluidics system 212 may, for example, be adapted to supply a fluid (e.g., a saline solution or air) into an eye to maintain its shape. In some implementations, the fluid may be injected into an eye at approximately 0.58 psi, although pressures up to 2.3 psi may be possible. The infusion fluid may be delivered to the eye through an infusion system like system 100. Typically, the infusion fluid is delivered throughout a surgery as the eye may steadily lose fluid (e.g., due to incisions). The fluidics system may include a pump and a fluid source, which may be managed by a computer system, such as computer system 204.

The different systems in console 200 may include control circuits for the operation and control of the various functions and operations performed by the console 200, such operations of a probe. Computer system 204 may be operable to govern the interaction and relationship between the different systems to properly perform a surgical procedure. To do this, computer system 204 may include one or more processors, one or more memory devices, and may be configured or programmed to control operations of the console 200, for example, based upon pre-established programs or sequences.

Figure 3:
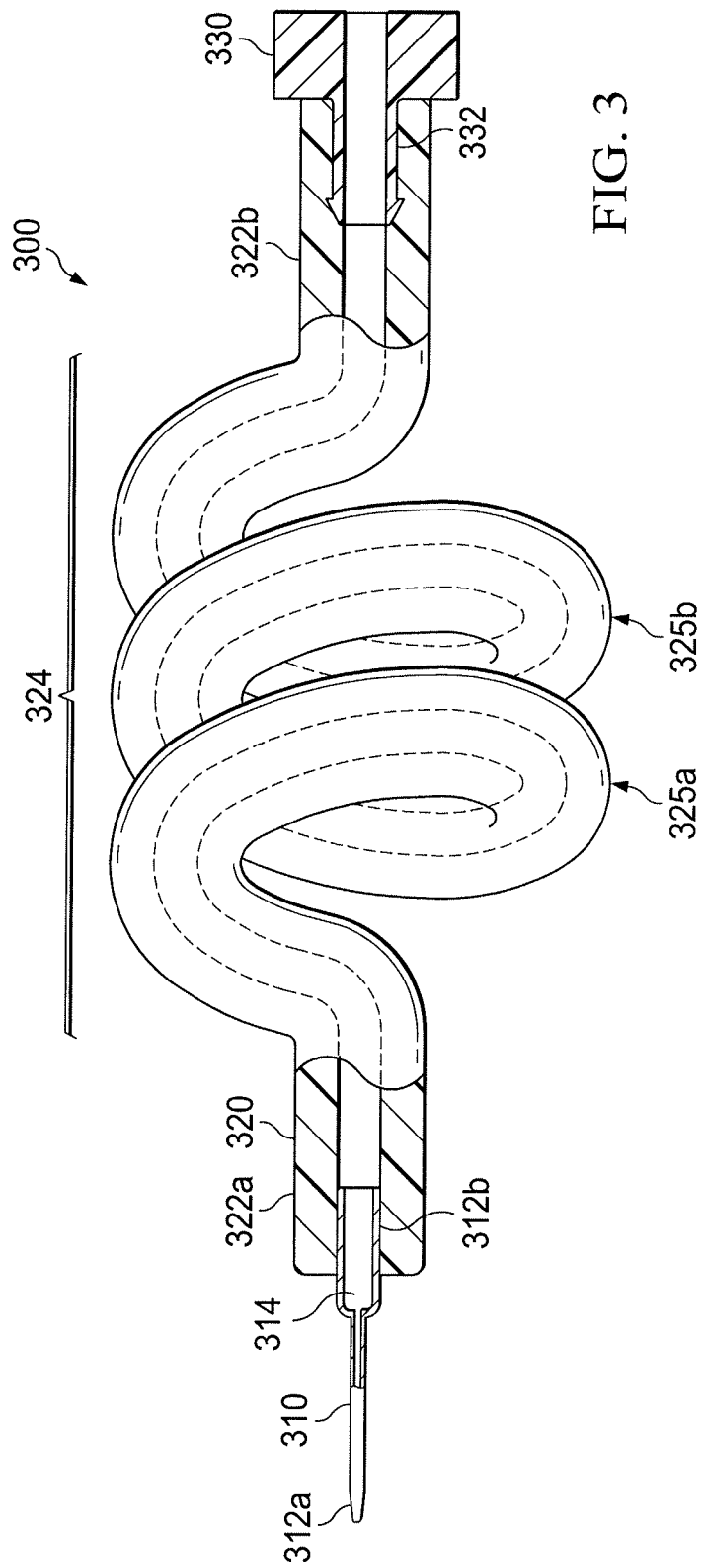
FIG. 3 shows another example system for ocular infusion.

FIG. 3 illustrates another example system 300 for ocular infusion. System 300 includes an ocular tip 310, a length of flexible tubing 320, and a coupler 330. System 300 may, for example, be useful for infusing a fluid (i.e., liquid or gas) into a patient's eye during surgery to maintain the eye's shape.

Ocular tip 310 includes a first portion 312a that is adapted to be inserted into an eye—directly or through another device (e.g., a trocar cannula). Second portion 312b is wider than first portion 312a and is adapted to couple to flexible tubing 320. The insides of first portion 312a and second portion 312b form a passage 314. Passage 314 allows infusion fluid to flow through ocular tip 310 into an eye.

Ocular tip 310 may be made of various materials. In particular implementations, for example, ocular tip 310 may be made of metal or hypodermic tubing. In other implementations, ocular tip 310 may be made of any other appropriate materials.

In certain implementations, ocular tip 310 may introduce fluid into an eye through a trocar cannula. In these implementations, one or more portions of ocular tip 310 (e.g., first portion 312a) may be sized to fit inside a trocar cannula, and another portion (e.g., second portion 312b) may be sized to abut the trocar cannula. In some implementations, ocular tip 110 may introduce fluid directly into an eye (e.g., by first portion 312a being inserted through the sclera).

Flexible tubing 320 includes a first end 322a, which is coupled to ocular tip 310 (e.g., by a friction fit), a second end 322b, which is coupled to coupler 330, and a coiled portion 324. The first end 322a may include a flange (e.g., a flange similar to flange 160) extending from a distal end thereof. The flange may prevent the ocular tip 310 from extending too far into the eye. As illustrated, coiled portion 324 includes two coils 325a, 325b. Coils 325a, 325b are set in flexible tubing 320, meaning that the coils 325a, 325b exist when flexible tubing 324 is in a quiescent state. Coiled portion 324 may include fewer or additional coils in other implementations.

Flexible tubing 320 may be composed of various materials. In particular implementations, flexible tubing 320 may be composed of a material with thermal set properties (e.g., silicone). In other implementations, flexible tubing 320 may be composed of any other appropriate flexible material.

Coupler 330 is adapted to couple to flexible tubing 320 and to a fluid source (e.g., a fluid source included with or access via a surgical console). Thus, the coupler 330 may be coupled to a surgical console, such as console 200, in order to couple to a fluid source. Coupler 330 includes an engagement mechanism 332 that engages second end 322b of flexible tubing 340 to prevent it from moving away from coupler 330. In this implementation, engagement mechanism 332 includes an elongated barb 335 that fits inside second end 322b. In other implementations, engagement mechanism 332 may have other configurations.

Coupler 330 may be composed of various materials. In particular implementations, coupler 330 may be composed of nylon. In other implementations, coupler 150 may be composed of any other appropriate material.

In certain modes of operation, system 300 assists with infusing a fluid (e.g., saline solution or air) into an eye as surgery proceeds. The infusion fluid may, for example, be supplied by a surgical console. For example, infusion fluid may be supplied by example console 200. However, other surgical consoles are within the scope of the disclosure. The amount of infused fluid may, for instance, be established by a user (e.g., a physician or other medical personnel).

During or after surgery, system 300 may also assist with placing another fluid into (e.g., air or silicone oil) into the eye, such as a tamponade fluid, to facilitate holding components (e.g., the retina) in place. Example tamponade fluids include silicone oil, air, or any other suitable tamponade fluid. Additionally, system 300 may provide a venting path during silicone oil injection.

System 300 has a variety of features. For example, system 300 assists in maintaining intraocular eye pressure, which prevents an eye undergoing surgery from collapsing. As another example, system 300 may provide increased room for a user to operate during a surgery. During certain surgeries, a user may have to manipulate an eye (e.g., to reach various locations). Previous infusion systems, which typically stick straight out of the eye, limited the room to perform such operations. Coils 325a and 325b, however, provide increased room for manipulation. Additionally, the coiled nature of flexible tubing 320 may allow ocular tip 310 to be placed at varying orientations without increasing torque on the eye.

Although FIG. 3 illustrates one implementation of a system for ocular infusion, other systems for ocular infusion may have fewer, additional, and/or a different arrangement of components. In particular implementations, first end 322a and/or second end 322b could include a long, straight portion. As another example, a system may not include coupler 330. For instance, flexible tubing 320 may couple to a surgical console. As an additional example, a system may include a coupler and second tubing, which may, for example, be a length of straight tubing. As a further example, ocular tip 310 may have other configurations.

FIGS. 4A-C illustrate an example system 400 for ocular infusion in use. System 400 includes an ocular tip 410, a length of flexible tubing 420, and a trocar cannula 440, which is shown inserted in an eye 450 through sclera 452. System 400 may, for example, be useful for infusing a fluid (i.e., liquid or gas) into eye 450 during surgery to maintain the eye's shape.

Ocular tip 410 includes a first portion 412a, a second portion 412b, and a third portion 412c, and may be similar to ocular tip 112 in system 100. First portion 412a is adapted to be inserted inside trocar cannula 440, and second portion 412b is wider than first portion 412a and also adapted to be inserted inside the trocar cannula. Third portion 412c is wider than second portion 412b and is sized to abut trocar cannula 440. Ocular tip 410 includes a passage (not visible) that is formed by the insides of portions 412a, 412b, and 412c. The passage allows infusion fluid to flow through ocular tip 410 and into eye 450.

Ocular tip 410 may be made of various materials. In particular implementations, for example, ocular tip 410 may be made of metal (e.g., stainless steel, titanium, gold, or any other suitable metal). In other implementations, ocular tip 410 may be made of any other appropriate material, such as, for example only, any suitable polymer.

Ocular tip 410 may be made by various processes. In certain implementations, for example, ocular tip 410 may be made by being drawn from a stock piece. The drawing process may create the necking between adjacent portions 412a, 412b, 412c. In other implementations, ocular tip 410 may be made by other processes.

Flexible tubing 420 is coupled to ocular tip 410 at one end. Flexible tubing 420 may have a variety of sizes and be composed of various materials (e.g., those with thermal set properties). Flexible tubing 420 may also include a number of coils that are set in the tubing. Thus, flexible tubing 420 may be similar to flexible tubing 120 or flexible tubing 320.

Trocar cannula 440 includes a tubular section 442 and a hub 444. Tubular section 442 serves as a port for introducing various fluids and/or devices to eye 450. One end of the tubular section is adapted to be inserted into eye 450, and hub 444 is coupled to the other end of the tubular section. Hub 444 prevents tubular section 442 from being inserted too far into eye 450. Hub 444 may, for example, be made of plastic. In other instances, the hub 444 may be made of any other suitable material.

Although FIG. 4 illustrates one implementation of a system for ocular infusion, other implementations of systems for ocular infusion may have fewer, additional, and/or a different arrangement of components. For example, ocular tip 410 may have other configurations (e.g., angled). As another example, flexible tubing 420 may have various configurations. Additionally, trocar cannula 440 may not be used.

The various implementations discussed and mentioned herein have been used for illustrative purposes only. The implementations were chosen and described in order to explain the principles of the disclosure and the practical application and to allow those of ordinary skill in the art to understand the disclosure for various implementations with various modifications as are suited to the particular use contemplated. Thus, the actual physical configuration of components may vary. For example, the mentioned size(s) of components and their illustrated sizing relative to each other may vary based on application. Moreover, the shapes of one or more components may vary depending on application. Thus, the illustrative implementations should not be construed as defining the only physical size, shape, and relationship of components.

The terminology used herein is for the purpose of describing particular implementations only and is not intended to be limiting. As used herein, the singular form "a", "an", and "the" are intended to include the plural forms as well, unless the context clearly indicates otherwise. It will be further understood that the terms "comprises" and/or "comprising," when used in the this specification, specify the presence of stated features, integers, steps, operations, elements, and/or components, but do not preclude the presence or addition of one or more other features, integers, steps, operations, elements, components, and/or groups therefore.

The corresponding structure, materials, acts, and equivalents of all means or steps plus function elements in the claims below are intended to include any structure, material, or act for performing the function in combination with other claimed elements as specifically claimed. The description of the present implementations has been presented for purposes of illustration and description, but is not intended to be exhaustive or limited to the implementations in the form disclosed. Many modifications and variations will be apparent to those of ordinary skill in the art without departing from the scope and spirit of the disclosure. The implementations were chosen and described in order to explain the principles of the disclosure and the practical application and to enable others or ordinary skill in the art to understand the disclosure for various implementations with various modifications as are suited to the particular use contemplated.

A number of implementations have been described for ocular infusion, and several others have been mentioned or suggested. Moreover, those skilled in the art will readily recognize that a variety of additions, deletions, modifications, and substitutions may be made to these implementations while still achieving ocular infusion. Thus, the scope of the protected subject matter should be judged based on the following claims, which may capture one or more concepts of one or more implementations.

The invention claimed is:

1. An ocular infusion system, the system comprising:
   a length of flexible tubing, the tubing adapted to convey an ocular infusion fluid and comprising a plurality of coils set in at least a portion thereof; and
   a tip adapted to be inserted into an eye, the tip coupled to a first end of the flexible tubing and adapted to convey ocular infusion fluid from the flexible tubing into the eye, the tip comprising:
      a first portion adapted to be inserted into the eye and a second portion adapted to remain outside the eye, wherein the second portion comprises a tubular member defining a lumen having a bend of approximately 90 degrees and a flange integrally formed with the tubular member that limits insertion of the first portion into the eye, the first portion being inserted at least partially into an opening of the second portion,
   wherein the first portion comprises a proximal segment having a proximal passage, a middle segment having a middle passage, and a distal segment having a distal passage, the distal passage having an internal diameter that is smaller than an internal diameter of the middle passage, the internal diameter of the middle passage being smaller than an internal diameter of the proximal passage, the internal diameter of the proximal passage being larger than an internal diameter of a passage of the second portion, the proximal segment connected to the middle segment by a first shoulder that is perpendicular to a central axis of the first portion, the middle segment connected to the distal segment by a second shoulder that is perpendicular to the central axis of the first portion, and the proximal, middle, and distal passages each having parallel internal sidewalls,
   wherein the first shoulder and the second shoulder are formed by an exterior surface of the first portion.

2. The system of claim 1, wherein the flexible tubing is composed of silicone.

3. The system of claim 1, wherein the flexible tubing comprises a first straight portion formed at a first end of the coiled portion and a second straight portion formed at a second end of the coiled portion.

4. The system of claim 1, wherein:
   the first portion is composed of metal; and
   the second portion is composed of plastic.

5. The system of claim 1, further comprising:
   a second length of flexible tubing; and
   a coupler adapted to couple to a second end of the first length of flexible tubing and to a first end of the second length of flexible tubing.

6. The system of claim 1, wherein the flange defines suture plates adapted to secure the second portion to the eye.

7. The system of claim 1, wherein the first portion is retained within the second portion by an interference fit.

8. The system of claim 1, wherein the second portion includes an internal annular recess adapted to receive the first portion.

9. The system of claim 1, wherein the length of flexible tubing is a first length of tubing, and further comprising a second length of flexible tubing coupled to the first length of tubing on an opposite end of the first length of tubing from the tip.

10. The system of claim 1, wherein the distal segment of the first portion of the tip terminates in a leading edge having a circular cross-sectional profile.

11. An ocular infusion system, the system comprising:
   a first length of flexible silicone tubing, the tubing adapted to convey an ocular infusion fluid and comprising a plurality of coils set in at least a portion thereof; and a tip adapted to be inserted into an eye, the tip coupled to a first end of the flexible tubing and adapted to convey ocular infusion fluid from the flexible tubing into an eye, the tip comprising:
  a first portion composed of metal and comprising:
    a distal portion adapted to be inserted into an eye;
    a proximal segment comprising a proximal passage;
    a middle segment comprising a middle passage;
    a distal segment comprising a distal passage;
    a first shoulder formed by an exterior surface of the first portion and connecting the proximal segment to the middle segment; and
    a second shoulder formed by the exterior surface of the first portion and connecting the middle segment to the distal segment; and
    a proximal portion defining a mounting interface, and
  a second portion composed of plastic and adapted to remain outside the eye, the second portion comprising a bend of approximately 90 degrees and an integrally formed flange that limits insertion of the first portion into the eye, wherein the second portion further comprises an annular recess, the mounting interface of the first portion being at least partially retained within the annular recess of the second portion, the annular recess being adapted to receive the second portion;
a second length of flexible silicone tubing;
a coupler adapted to couple to a second end of the first length of flexible tubing and to a first end of the second length of flexible tubing; and
a second coupler adapted to couple to a second end of the second length of flexible tubing.

12. The system of claim 11, wherein the flange extends from the second portion.

13. The system of claim 11, wherein the first length of flexible tubing comprises a first straight portion formed between the first end of the first length of tubing and the coiled portion, and a second straight portion formed between the coiled portion and the second end of the first length of tubing.

14. The system of claim 11, wherein the proximal segment comprises a proximal internal sidewall,
  wherein the middle segment comprises a middle internal sidewall, and
  wherein the distal segment comprises a distal internal sidewall,
  wherein the distal passage has an internal diameter that is smaller than an internal diameter of the middle passage,
  wherein the first shoulder is transverse to a central axis of the first portion,
  wherein the internal diameter of the middle passage is smaller than an internal diameter of the proximal passage,
  wherein the second shoulder is transverse to the central axis of the first portion,
  wherein the proximal internal sidewalls, middle internal sidewalls, and distal internal sidewalls being parallel, and
  wherein the internal diameter of the proximal passage is larger than an internal diameter of a passage of the second portion.

15. The system of claim 14, wherein the first shoulder is perpendicular to the central axis of the first portion of the tip, and wherein the second shoulder is perpendicular to the central axis of the first portion of the tip.

* * * * *